United States Patent [19]

Hoyt

[11] Patent Number: 4,936,682
[45] Date of Patent: Jun. 26, 1990

[54] INSTRUMENT FOR INDEPENDENTLY AND KINETICALLY MEASURING LIGHT TRANSPASSION THROUGH A PLURALITY OF SAMPLES

[75] Inventor: Joshua K. Hoyt, Woods Hole, Mass.

[73] Assignee: Associates of Cape Cod, Inc., Falmouth, Mass.

[21] Appl. No.: 84,098

[22] Filed: Aug. 11, 1987

[51] Int. Cl.⁵ ..................... G01N 21/27; G01N 21/31
[52] U.S. Cl. ........................... 356/414; 250/576; 356/440; 356/39
[58] Field of Search .............. 356/440, 409, 416, 414, 356/39, 244; 250/576

[56] References Cited

U.S. PATENT DOCUMENTS

| | | | |
|---|---|---|---|
| Re. 31,108 | 12/1982 | Ginsberg et al. | 422/64 |
| 3,041,146 | 6/1962 | Kuzell. | |
| 3,141,948 | 7/1964 | Young. | |
| 3,267,364 | 8/1966 | Page et al. | |
| 3,522,436 | 8/1970 | Posgate. | |
| 3,746,864 | 7/1973 | Tick et al. | |
| 3,811,780 | 5/1974 | Liston | 356/409 X |
| 3,873,273 | 3/1975 | Moran et al. | 356/246 |
| 3,877,817 | 4/1975 | Ralston. | |
| 3,890,510 | 6/1975 | Sturm | 250/565 |
| 3,905,482 | 9/1975 | Knulst | 356/246 |
| 3,918,817 | 11/1975 | Posgate | 250/574 |
| 3,964,867 | 6/1976 | Berry | 356/246 |
| 3,977,794 | 8/1976 | Liedholz | 356/244 |
| 4,038,555 | 7/1977 | Freeman | 250/573 |
| 4,055,395 | 10/1977 | Honkawa et al. | 356/244 |
| 4,061,469 | 12/1977 | DuBose | 356/39 X |
| 4,213,764 | 7/1980 | O'Connor | 250/574 |
| 4,257,708 | 3/1981 | Fukuda | 356/435 |
| 4,276,383 | 6/1981 | Leighton et al. | 435/291 |
| 4,285,906 | 8/1981 | Meltzer et al. | 422/64 |
| 4,448,534 | 5/1984 | Wertz et al. | 356/435 |

FOREIGN PATENT DOCUMENTS

| | | | |
|---|---|---|---|
| 0173021 | 3/1986 | European Pat. Off. | |
| 55-76940 | 6/1980 | Japan | 356/426 |
| 159162 | 7/1986 | Japan. | |

OTHER PUBLICATIONS

"Toxinometer ET-201", Wako Pure Chemical Industries, Ltd., Osaka, Japan.
"The Lal Update", Associates of Cape Cod, Inc., Woods Hole, MA, vol. 4, No. 2, Jun. 1986.
"The LAL-4000 Automatic Endotoxin Detection System", Associates of Cape Cod, Inc., Woods Hole, MA.
"MS-2 Microbiology System and Research System", cover letter, Abbott Laboratories, Irving, TX.
"The LAL-4000 Automatic Endotoxim Detection System", Pyrotell Benthos Clinical Systems, North Falmouth, MA.

(List continued on next page.)

Primary Examiner—Vincent P. McGraw
Attorney, Agent, or Firm—Oblon, Spivak, McClelland, Maier & Neustadt

[57] ABSTRACT

An analytic instrument for kinetically measuring light absorption characteristics of a plurality of independent samples contained in disposable test tubes arranged in a circular pattern about a single light source. The instrument is designed to be used with a host personal computer and is not specific to any particular type of assay. The instrument obtains and temporarily stores raw data in the form of digitized output signals from the plurality of photodetectors and periodically passes them to the host computer. An incubator has test tube wells arranged in a circular array equidistant from a single incandescent light source. The circular symmetry controls the thermal gradients in the incubator such that all of the samples are disposed on the same isotherm and all of the photodetectors are disposed on the same isotherm. The instrument is designed for use with disposable test tubes, and sources of error arising from optical variation in such test tubes are minimized by providing a separate detector for each tube and by holding the tube fixed with respect to the detector. The light output from the single light source is continuously monitored and is kept constant.

19 Claims, 8 Drawing Sheets

OTHER PUBLICATIONS

"MS-2 A Rapid Automated Microbiology System for Urine Testing", Abbott Laboratories, Irving, TX.

"MS-2 Microbiology System, Now You Get Answers, Not Just Clues", Abbott Laboratories, Irving, TX.

Levin, J. et al., "Clottable Protein in Limulus: Its Localization and Kinetics of Its Coagulation by Endotoxin", *Throb. Diath. Haemorrh.*, 19:186–197 (1968).

Jorgensen, J. H., et al., "Automation of the Limulus Amoebocyte Lysate Test by Using the Abbott MS-2 Microbiology System", *Appl. Environ. Microbiol.* 41:1316–1320.

Oishi, H., et al., "Automated Limulus Amoebocyte Lysate (LAL) Test for Endotoxin Analysis Using a New Toxinometer ET-201", *J. Parenter. Sci. Technol.*, 39:194–199.

Novitsky, T. J., et al., "Automated LAL Testing of Parenteral drugs in the Abbott MS-2", *J. Parenter. Sci. Technol.*, 36:11–16 (1982).

Novitsky, T. J., et al., "Design Criteria and Evaluation of the LAL-4000 for Kinetic Turbidimetric LAL Assay", *Detection of Bacterial Endotoxins With The Limulus Amebocyte Lysate Test*, Proceeding Woods Hole Conf. On Endotoxin (1985).

INSTRUMENT FOR INDEPENDENTLY AND KINETICALLY MEASURING LIGHT TRANSPASSION THROUGH A PLURALITY OF SAMPLES

BACKGROUND OF THE INVENTION

1. Field of the Invention

The instrument relates to conducting assays by kinetically measuring changes in light transmission through a plurality of samples contained in test tubes and, more particularly, the invention provides an inexpensive desktop instrument that may advantageously be used with a standard personal computer for conducting such assays.

2. Discussion of the Background

FIG. 1 is a perspective view of a prior art system including a personal computer 1 (IBM PC or PC-compatible), a printer 2 connected to the personal computer, a CRT monitor 3, and an instrument 4 known commercially as the LAL-4000. The LAL-4000 is specially adapted for performing an assay generally known as the LAL assay, which is a quantitative assay for bacterial endotoxins. Sample and a reagent are mixed in a disposable test tube 10 and incubated at 37° C. No additional reagents, dyes or acids are required.

Prior to the development of the LAL-4000, the LAL assay was traditionally performed as a gel-clot test. In contrast, the assay as conducted using the LAL-4000 is a kinetic assay. The main distinction between the two methods is the manner in which the test is read. The gel-clot method is dependent upon the formation of a firm gel produced by the LAL components in response to the presence of endotoxins, while the kinetic turbidimetric method uses the increase in turbidity which preceeds gel formation as the basis for quantitation. Conducting the traditional gel-clot method depended upon reaching an end point of gel formation and required a substantial period of time to conduct, including a one hour incubation period. Interpreting the results involved a subjective judgment by the tester as to whether or not a gel had formed. In contrast, the kinetic assay provides a continuous measurement according to which the LAL-4000 measures the time required for samples to reach a specific level of turbidity that is achieved prior to the end point of gel formation. This time is referred to as the "onset time". The assay is essentially complete once the sample under test has attained an onset time or has incubated for a predetermined time period corresponding to a specific level of endotoxin.

A kinetic assay has several advantages over the end point gel-clot assay employing a fixed incubation period. These advantages include increased sensitivity, greater resolution, greater precision, the elimination of subjectivity in interpreting the results, and increased assay speed.

The LAL-4000 unit includes a fixed incubator block 6 in the form of a rectangular solid having a plurality of test tube wells 8 disposed in a rectangular array. The instrument was designed to use disposable test tubes of non-optical quality. A separate pulsed LED light source 12 and photodetector 14 (FIG. 2) are provided for each test tube, so that light from one of the LED's 12 shines through a sample in its associated test tube and impinges on the associated photodetector 14. Because a separate light source is used for each test tube (and therefore for each data channel), variability from one light source to the next presents problems in interpreting the collected data to obtain quantified results. The size and weight of the instrument 4 are increased because of the need to provide electric power to each of a plurality of light sources. Furthermore, because of the rectangular array in which the test tubes, light sources and photodetectors are disposed, it is difficult to service the photodetectors and light sources.

In the LAL-4000, each photodetector 14 corresponds to a data channel. The instrument handles the data channels independently, so that the measuring for each data channel may begin at a separate time. Each test begins when a test tube 10 is inserted into a well 8. Each detector 14 is placed lower than its corresponding light source, so that it does not receive light from the associated light source 12 unless a test tube is present, and the instrument relies on detecting light refraction through the lower portion of the test tube in order to determine that a test tube has been inserted. Because of the low quality and internal variability of the non-optical quality glass used in the disposable test tubes, the distorted light path through the test sample is sensitive to jarring. This problem is further compounded where, as in the LAL-4000, the optical path passes through the curved lower portion of the test tube, where the refracted light path is especially poor. At times, a significant period of time has elapsed before it has been discovered that the instrument had failed to detect the presence of a test tube and had not begun collecting data at the appropriate time.

Because the LAL-4000 is designed with the light path passing through the bottom of non-optical quality test tubes, the sensitivity of the instrument to vibration and jarring is increased. In addition, inherent variability in the spectral outputs of the separate light sources forces one to conduct a substantial amount of pre-screening of the components to be used. This added complexity detracts from the design of the LAL-4000.

The LAL-4000 provides twenty test tube wells 8, this number being expandable to forty by re-working the chassis at substantial cost.

Because of the physical configuration of the incubator block 6, the range of assays that may be conducted is limited to assays capable of using light at the wavelengths provided by the individual LED light sources. This is because of the impracticality of changing each light source and because of the inability to insert a light filter between each light source and each sample.

The LAL-4000 uses a commercially available power supply which provides +/−15VDC, +12VDC, and +5VDC regulated voltages. It further uses a commercial computer board set (four boards minimum: CPU, an analog to digital converter, an input/output board, and an analog interface). Additional circuit boards are required to sense and measure the changes in light transmission within the incubator. These separate boards are electronically connected with extensive wiring harnesses which are expensive to make and install and are prone to failure. The LAL-4000 is approximately twenty inches wide, eighteen inches deep and eight inches high. It has a volume of 3000 cubic inches and weighs 42 pounds.

The LAL-4000 communicates with its host computer through a standard RS-232 interface. It sends data to the host computer only when a predetermined change in light transmission is measured in a given well. This forces the data string to include the well identity and the time of the measured change, in addition to the actual magnitude of the change itself. Since the logic circuitry of the LAL-4000 determines what data is transmitted and when, the data is not in a predetermined, regular format, and its utility for a variety of purposes is diminished accordingly.

Shown in FIG. 2 is a diagrammatic top view of the incubator block 6 of the LAL-4000, showing the general locations of the test tube wells 8, the individual light sources 12 and the photodetectors 14. Also shown, in dashed lines, are isotherms 16. As noted above, a heater is provided to maintain the incubator block at substantially 37° C. Accordingly, the center of the block is at a somewhat higher temperature than the edge portions of the block. Because of the rectangular array in which the test tubes 10 are disposed, there necessarily results a variation in temperature among the various samples under test. Such thermal gradients within the incubator have a detrimental effect on the assay. The temperature in a given well affects the speed at which the reaction takes place. Any such variablility affects the intercomparison of results. Accordingly, this variation further detracts from the reproducibility of the results.

The temperature variations within the incubator block also are experienced by the photodetectors 14. All photovoltaic devices have substantial temperature coefficients. For a given incident light, the current generated by the sensor 14 is a strong function of its ambient temperature. Accordingly, these temperature variations among the photodetectors even further adversely affect the reproducibility of the results.

Other instruments for making turbidimetric mesurements are known, including the Wako Toxinometer, Abbott Laboratories MS-2 ®, General Diagnostics Coagamate, and a microplate reader, also called a micro-titer plate reader. The Toxinometer, the MS-2 and the microplate reader employ a rectangular grid of test tube wells or sample-containing cuvettes. Like the LAL-4000, the Toxinometer has relatively inaccessible electronic parts within the heater block and is a simple single-wavelength optical reader. Like the LAL-4000, the Toxinometer has wells arranged in a grid. Consequently, attempts to control the incubator temperature result in strong temperature gradients.

Like the LAL-4000, the Toxinometer and the MS-2 each have a separate light source for each sample well. Other instruments, including the Coagamate, employ a circular geometry, a single light source, and light detecting means which are not dedicated to a particular sample.

The Coagamate uses a carousel. This requires the use of optical grade cuvettes, because the optical path through a disposable tube on a moving carousel cannot be consistently established on a repeatable basis. Furthermore, a moving carousel is difficult to incubate because of poor heat transfer to the moving parts. The agitation caused by the movement of the carousel has a detrimental effect on the repeatability of the assay.

One additional characteristic of the microplate reader is that all the samples must be prepared at one time. The tests are not independently initiated.

SUMMARY OF THE INVENTION

Accordingly, one object of the current invention is to provide a novel instrument for independently and kinetically measuring the light absorption characteristics of a plurality of samples contained in disposable test tubes arranged in a substantially circular pattern about a single light source.

It is a further object of the current invention to enhance the accuracy and repeatability of an instrument for conducting turbidimetric and colorimetric measurements having the above characteristics by providing a single controlled light source for all data channels.

It is an additional object of the current invention to provide an instrument having the above characteristics and having an incubator capable of use with a variety of standard sizes of non-optical grade test tubes.

It is yet a further object of the current invention to provide an analytic instrument offering enhanced repeatability by continuously monitoring and correcting for variability in light from a single measuring light source due to physical changes in the light source or power supply.

It is a still further object of the current invention to provide an analytic instrument affording reduced complexity and ease of maintenance with respect to light generating and measuring circuitry.

A yet additional object of the current invention is to provide an instrument capable of performing the known LAL assay and that is easily capable of performing other turbidimetric and colorimetric assays.

It is an object of the current invention to provide enhanced repeatability and accuracy of an analytic instrument by achieving uniformity of temperature among the samples and uniformity of temperature among the photodetectors.

A still further object of the current invention is to provide an analytic instrument having great versatility, being adapted for use with an external computer and which relegates to the personal computer all or substantially all of the assay-specific data collection and analysis functions.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 3:
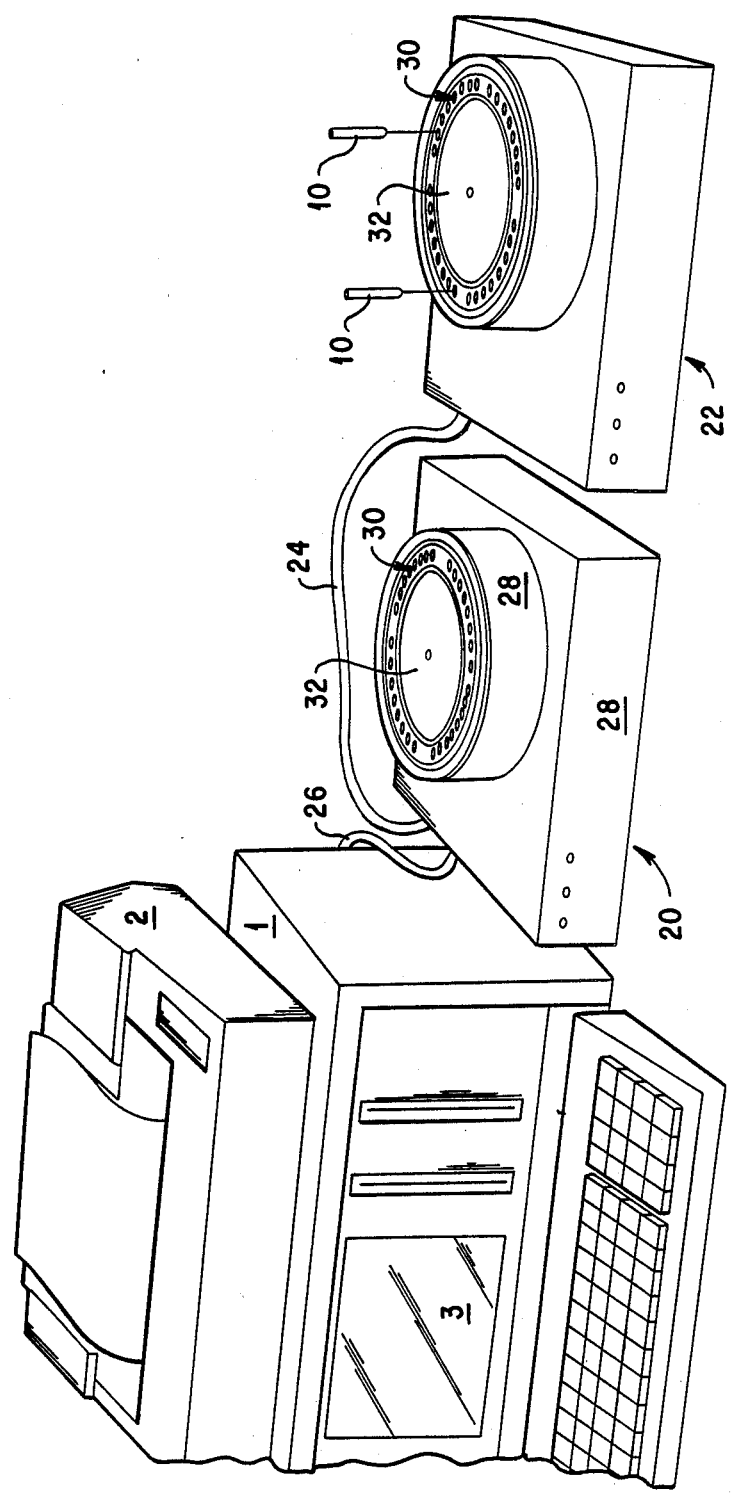
FIG. 3 is a pictorial representation of a typical system including an analytic instrument according to the current invention, the illustrated system including a master module and a single expansion module.

Referring now to the drawings, wherein like reference numerals designate identical or corresponding parts throughout the several views, and more particularly to FIG. 3 thereof, there is shown a system including a first module 20 and a second module 22 according to the current invention, the second module 22 being connected to the first module 20 by a first harness 24, the first module 20 being connected by a second harness 26 to a standard commercially available digital computer 1 having outputs in the form of a CRT 3 and a printer 2. The latter items are shown partly broken away for reasons of convenience relating to the scale of the Figure. Preferably, the computer is a microcomputer of a type that is readily available commercially and is inexpensive, such as an IBM PC or a PC-compatible computer.

Although the differences between the modules are not apparent from FIG. 3, the first module 20 is a master module, and the second module 22 is an expansion module, as will be described in more detail below. If desired, an additional expansion module may be connected to the master module.

Visible in FIG. 3 for each module is a housing 28, the top portion of an incubator 30 and a lid 32. As will also be described in more detail below, the electronic circuitry on-board the master and expansion modules is kept to a minimum, in order to provide an inexpensive instrument and to enhance the versatility of the first and second modules, to decrease the cost of the instrument (i.e., of the first and second modules) and also to make maximum use of the data processing capabilities of the personal computer. Accordingly, the current invention provides a relatively inexpensive yet versatile desktop instrument that may advantageously be used by a laboratory or the like having possession of a standard personal computer. However, it will be understood that, if desired, the functions performed by the personal computer may be incorporated into the housing of the master module, for example by using known techniques of large scale integration.

Figure 4:
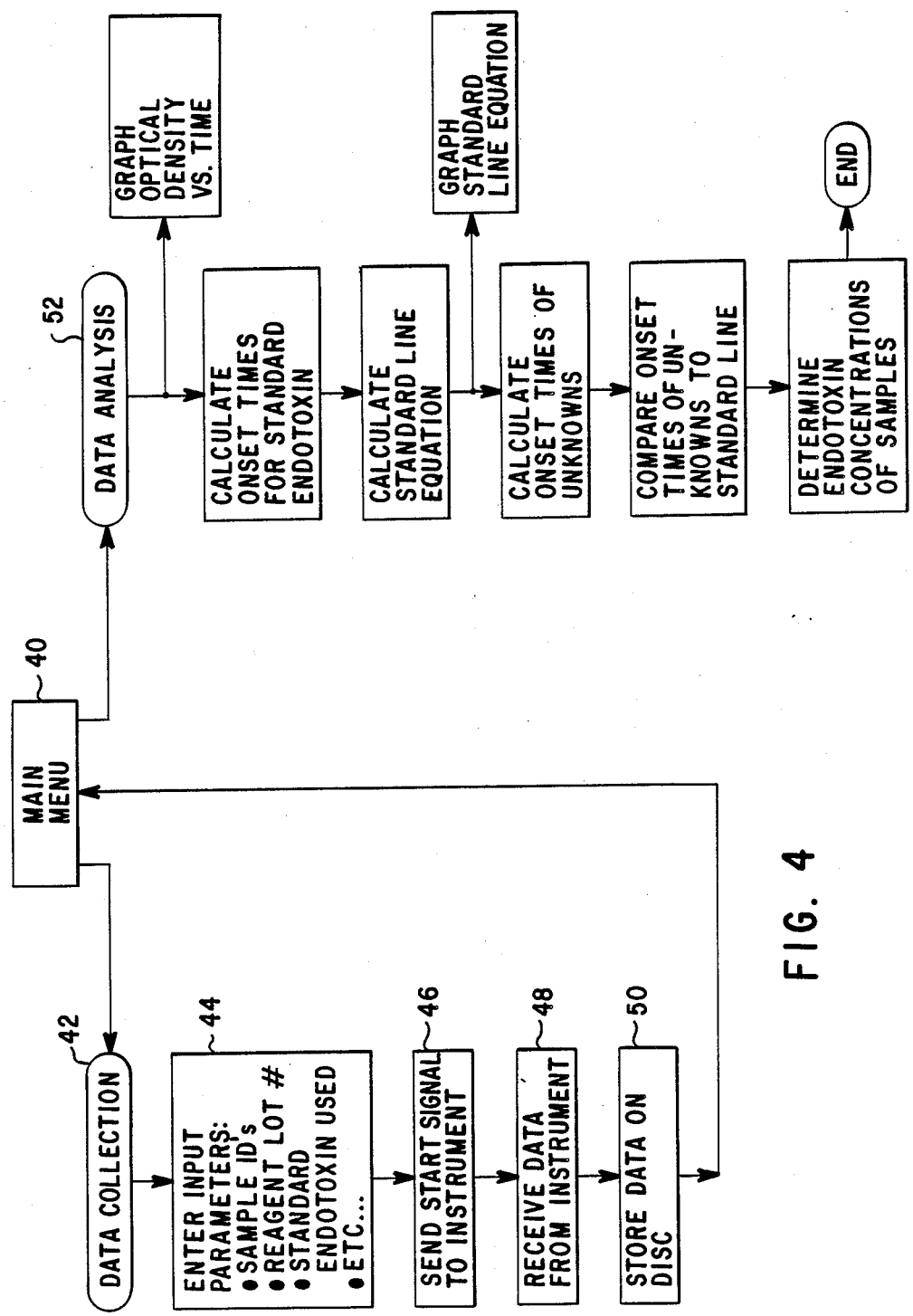
FIG. 4 is a flow chart of a representative example of applications software that will reside in a host computer when used with an analytic instrument according to the current invention, the flow chart showing by way of example typical functions used in performing a LAL assay.

FIG. 4 illustrates a flow chart of typical applications software that may be resident in the personal computer. This flow chart is presented by way of non-limiting example and forms no part of the current invention. However, some form of applications software of the type illustrated is highly desirable in order to make the highest use of an invention according to the current invention. The particular example set forth in FIG. 4 is a flow chart for collecting and analyzing data during the conduct of a LAL assay. Similar programs may be provided for conducting other types of assays.

Beginning with a main menu 40, the operator elects to proceed either with a data collection subroutine 42 or, if data collection already has occurred, with a data analysis subroutine 52. In the data collection subroutine 42, the user first, at block 44, enters various data in the form of input parameters such as the identifications of various samples to be associated with different test tube wells, the reagents used in those samples, and so forth. The user then sends a start instruction (block 46) to the master module, at which time the instrument according to the current invention performs its tasks, as will be described in more detail below. As the instrument is gathering data, it sends the data to the personal computer (at 48), the data then being stored on disk (at 50). Thereafter (or in real time if desired) the stored data is analyzed in the data analysis subroutine 52, and the results are displayed or printed out or both. Inasmuch as the instrument measures changes in light transmission through the samples, the data received by the program resident in the personal computer represents absolute values. From these absolute values, the host computer can calculate the percent change in light transmission that occurs as the kinetic assay proceeds.

A typical master module 20 will now be described with reference to FIGS. 5 and 6. Except where noted, the description can apply either to a master module 20 or to an expansion module 22.

Figure 5:
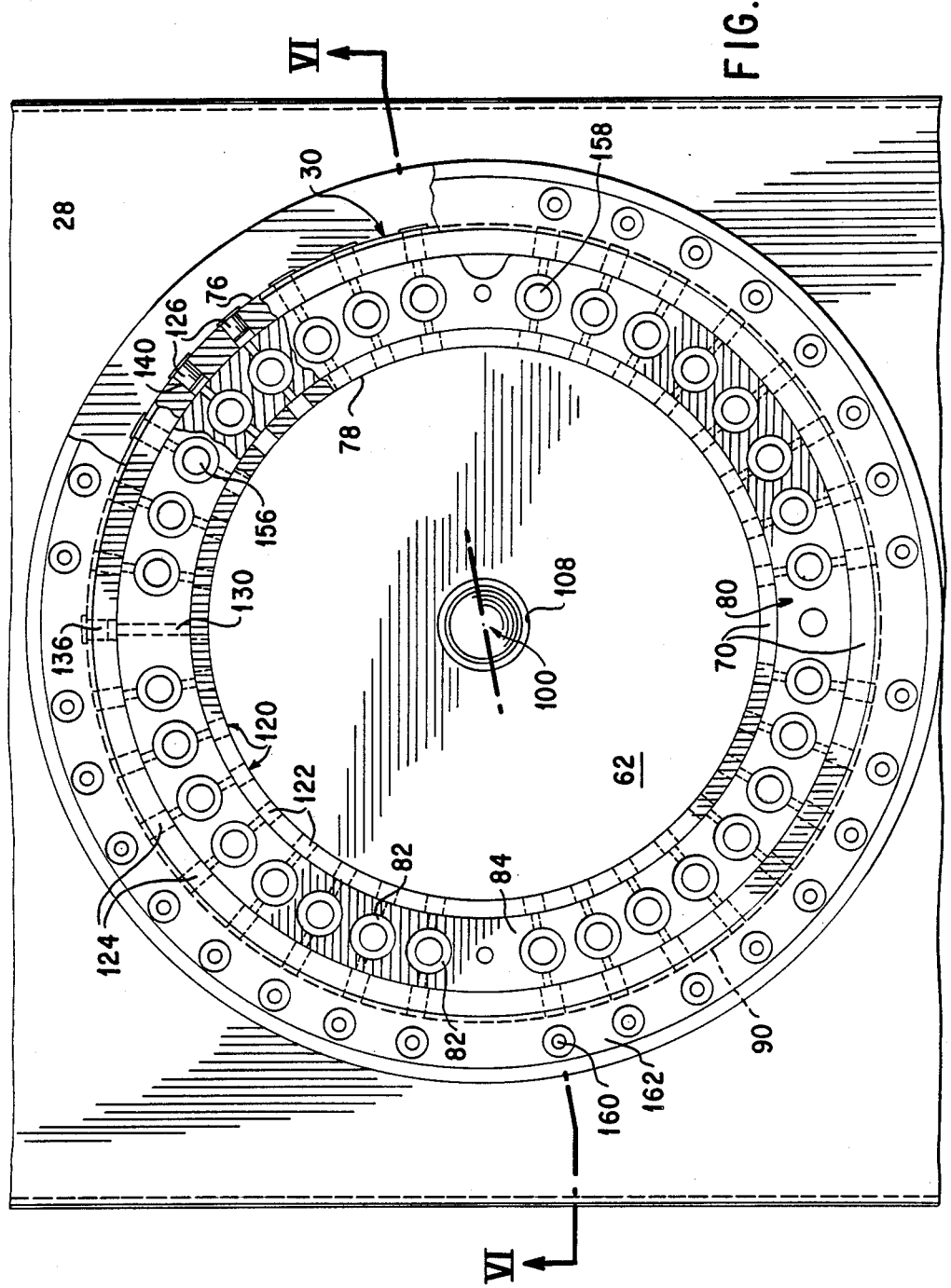
FIG. 5 is a top view of a preferred embodiment of a module, with the lid removed, the incubator shown partly in section and partly broken away, and the indicator ring and housing partly broken away.
Figure 6:
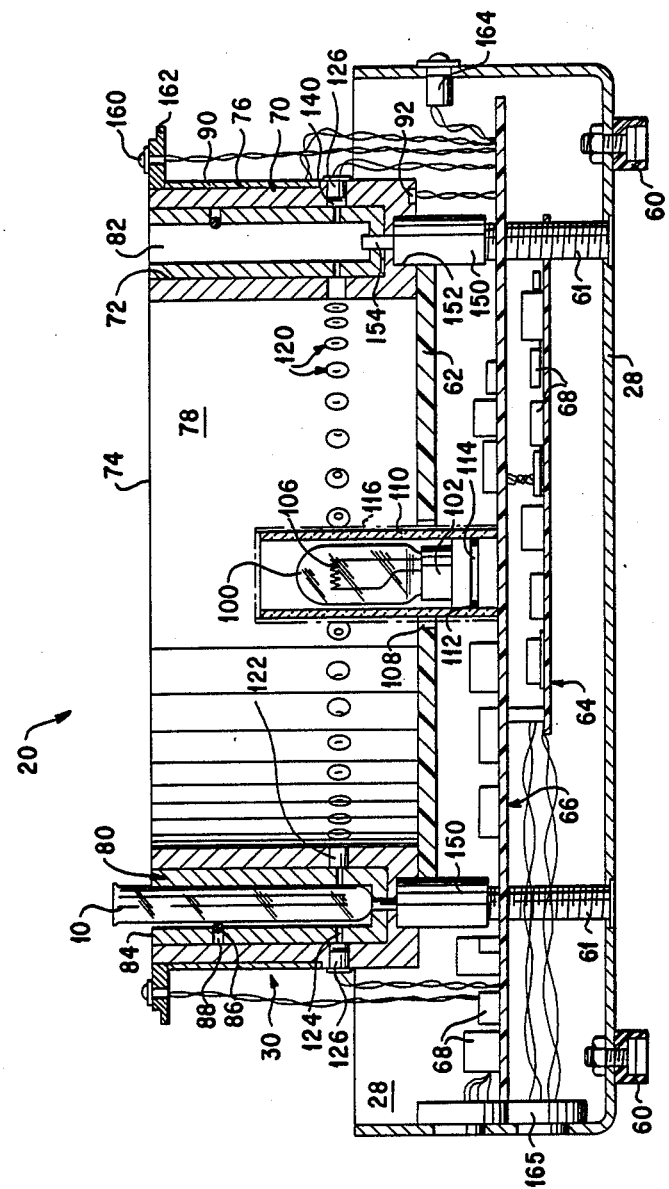
FIG. 6 is a front elevation, partly in section, of a preferred embodiment of a master module, with the lid and an upper portion of the housing removed, and with the incubator being shown along line VI—VI of FIG. 5.

In FIGS. 5 and 6, the lid 32 has been removed, and, in FIG. 6, an upper portion of the housing 28 is not shown. Preferably, the housing 28 is supported on rubber feet 60 to help isolate externally-imposed vibration. Four supports 61 fixedly mount the incubator 30 on a bottom surface of the housing. The spacers also mount a thermally insulating disk 62, made for example of Delrin® acetal resin, the insulator disk 62 being mounted intermediate the bottom portion of the housing and the incubator 30. The spacers 61 also mount an instrument controller board 64 and an auxiliary board 66. Both the instrument controller board 64 and auxiliary board 66 have electronic circuitry mounted thereon, as will be described in more detail below. In FIG. 6, this circuitry is represented in highly schematicized form by boxes 68. The only difference between a master module 20 and an expansion module 22 is that only the master module 20 has an instrument controller board 64 and associated electrical connections. All modules have an auxiliary board 66. The auxiliary board 66 forms a portion of module control means, as will be described in more detail below.

The incubator 30 serves as test tube support means and is substantially annular in shape. It comprises a heater block 70 and a test tube rack 80, both of which also are of substantially annular shape. In the preferred embodiment, the heater block 70 has an inside diameter of approximately 5.5 inches and an outside diameter of approximately 7.5 inches. It is made of a good thermal conductor such as aluminum. Formed in the heater block 70 is a receiving opening 72 in the form of an annular slot extending down from a top surface 74 of the heater block, the test tube rack 80 being closely received in the receiving opening 72 so that good thermal contact is provided between the heater block 70 and the test tube rack 80. A heater 90 is mounted circumferentially of the heater block 70, most preferably on either an outer 76 or inner 78 side wall of the heater block. Temperature sensing means such as a thermistor 92 are provided to sense the temperature of the heater block 70. Both the heater 90 and the temperature sensing means 92 are connected electrically with the auxiliary board 66.

The test tube rack 80 also is made of a good thermal conductor such as aluminum. Thirty-two test tube wells 82 are formed in a substantially circular array, the wells 82 extending downwardly from an upper surface 84 of the test tube rack. The wells are arranged in four groups of eight (spaced ten degrees apart), the groups being demarcated at the locations of the incubator supports 61.

According to one feature of the current invention, the user may advantageously be provided with at least two such test tube racks 80, the racks being of substantially the same construction except for the diameters of the test tube wells 82. In particular, the diameters of the wells 82 of one rack 80 will be substantially 10 mm, and the diameters of the wells 82 of the other rack 80 will be substantially 12 mm. These diameters correspond to the diameters of presently commercially available non-optical quality disposable laboratory test tubes. It will be understood that test tube racks 80 having other well diameters may be provided if such test tubes become available in other diameters in the future. It also will be understood that the well diameters "substantially" equal 10 mm and 12 mm, respectively, such that the wells are more than large enough to admit the majority of test tubes of those standard diameters, such test tubes presently being subject to great manufacturing tolerances. In a preferred embodiment, the minimum diameter of a well in the 10 mm range is 0.394 inches, and the maximum diameter of such a well is 0.399 inches. Also in the preferred embodiment, the minimum diameter of a well in the 12 mm range is 0.470 inches, and the maximum diameter of such a well is 0.475 inches.

Even where the diameters of the wells fall within the above-stated tolerance ranges, many of the highly-variable test tubes will be received with a loose fit and therefore will be subject to some displacement during the conduct of a test, due to random and variable externally-imposed jarring and vibration experienced by the instrument. Because of the typical variations in optical characteristics that occur from one point to another in any given one of these disposable test tubes, any such slight displacement can affect the readings and is therefore considered undesirable. Accordingly, means for preventing such displacement are provided. In the preferred embodiment, the means for preventing such displacement is a test tube retainer in the form of an elastic ring-like member 86 such as an O-ring disposed in a circular pattern radially beyond the circular array of test tube wells. The elastic ring-like member 86 is received in a slot 88 formed in and extending around an outer surface of the test tube rack. The slot 88 also extends radially inward from the outer surface of the test tube rack and intersects the wells 82. Accordingly, the test tubes 10 are biased against the interior walls of the wells 82 and are thus restrained against movement. Such biasing also has the beneficial effect of enhancing heat transfer between the test tube rack and the test tubes.

The module is provided with a single incandescent light source 100, which will be called a measuring light source because it provides the light used in measuring changes in light transmission through the samples. An important feature is that each of the test tube wells is equidistant from the measuring light source 100. In the preferred embodiment, the measuring light source is a single standard halogen bulb disposed at the center of curvature of the circular array of test tube wells. The bulb 100 is received in a standard commercial socket 102 that is fixed on the auxiliary board 66 and spaced therefrom by a spacer 104 which also is fixed on the auxiliary board 66. The spacer 104 has a height chosen such that the filament 106 of the measuring light source 100 will be at the approximate levels of light passages 120, 130 described below. A circular opening 108 is provided in the insulator disk 62 to provide a penetration for the measuring light source assembly. The measuring light source 100 draws electric power from the auxiliary board 66.

Other embodiments are possible, if desired. For example, an annular bulb may be used for the light source. Such an annular bulb also can be disposed such that the test tube wells are equidistant from it.

It is desirable, but not necessary, that some means be provided between the measuring light source 100 and the incubator 30 for diffusing the light from the measuring light source 100. In the preferred embodiment, such means are provided in the form of a cylindrical diffuser 110 made of sand-blasted glass. The diffuser 110 rests on the auxiliary board 66, is further supported by an O-ring 112 received in an annular slot 114 formed on an outer surface of the light spacer 104, and extends upwardly through the penetration opening 108 of the insulator disk 62. The substantially open construction of the preferred embodiment allows one to select a variety of alternative locations for the diffuser 110, if desired. For example, a cylindrical diffuser may be provided having a diameter slightly less than that of the inside diameter of the incubator 30 and resting on the insulator disk 62.

As noted above, an instrument according to the current invention may be used for conducting colorimetric measurements in addition to turbidimetric measurements. For the former purpose, a spectrally-selective light filter 116, shown in phantom, may be provided between the measuring light source 100 and the incubator 30 in a manner similar to that described above in regard to the diffuser 110. It has been found to be convenient to provide such a light filter 116 by rolling a sheet of theater gel into a cylindrical structure and inserting it into the penetration opening 108 of the insulator disk 62.

The incubator 30 is provided with thirty-two measuring light passages 120 that extend radially through both the heater block 70 and the test tube rack 80, substantially at the level of the filament 106 of the measuring light source 100. Each measuring light passage 120 intersects a test tube well 82 such that light from the measuring light source 100 will pass through a first portion 122 of a given measuring light passage 120, then pass through a sample contained in a test tube 10 disposed in the well 82, and then enter a second portion 124 of the measuring light passage 120.

Each measuring light passage 120 is provided with a separate measuring photodetector 126 positioned so as to intercept light from the measuring light source 100 after the light has passed through its associated well 82. For convenience, only some of the measuring photodetectors 126 are shown in FIG. 5.

In addition to the thirty-two measuring light passages 120, there is provided an additional light passage 130 and associated photodetector 136 that are not used in conducting measurements of test samples but are, instead, dedicated to controlling the intensity of the measuring light source 100, as will be described in detail below. The dedicated photodetector 136 and the measuring photodetectors 126 are electrically connected to the auxiliary board 66.

All of the photodectors 126, 136 are mounted on the incubator 30 in close thermal contact therewith. That is, the mounting of the photodetectors 126, 136 is such that the temperature of each photodetector is directly governed by heat transfer from the incubator 30 to the photodetector. Such mounting may be accomplished by providing a receiving aperture 140 at the end of each light passage 120,130 that is of an appropriate size to receive the corresponding photodetector 126, 136 with a press fit. This allows for good thermal conductivity between each photodetector and the incubator.

Thirty-two electromechanical switches 150 are fixed on the bottom of the incubator 30 at respective locations immediately beneath the individual test tube wells 82. In the preferred embodiment, the switches 150 are fixedly received in corresponding cut-outs 152 in the base of the heater block 70. Each switch 150 is provided with an actuator 154 that extends upwardly through a respective opening 156 (FIG. 5) in the heater block 70 and an opening 158 in the test tube rack 80, and further extends into the corresponding test tube well 82 in position for being contacted by a test tube 10 present within the well. The introduction of a test tube into a well will cause a change of state of the corresponding switch 150. Accordingly, each switch 150 is a well state indicating means for providing an independent signal for each well 82, indicating whether or not a test tube 10 is present in that well. These switches 150 are a part of the module control means, which will be described further below in connection with the description of the auxiliary board 66. The switches 150 are connected electrically to the auxiliary board 66.

Preferably, each electromechanical switch 150 is of the push-on/push-off type in which the actuator 154 is spring-loaded from within the switch and which is temporarily locked in its depressed position in toggle-like fashion by the switch when the switch is pushed on. In this way, the upward force of the spring within the switch does not tend to push the test tube upward during a measurement. Such switches are commercially available, for example, as part no. 401CQ of American Switch Corporation or Schurter part no. 0041.9302.7.3.

Because of the toggle-like action, each electromechanical switch 150 provides an immediate tactile feedback to a user when inserting a test tube 10 into a given well 82. Such feedback provides the operator with an indication that the instrument has sensed the presence of the test tube, and that measurement for that well has successfully been initiated.

An additional such immediate feedback is provided visually by an indicating LED 160 mounted beside each well 82. Thirty-two such indicating LED's, each electrically connected to the auxiliary board 66, are mounted on an indicator ring 162 which, in turn, is disposed circumferentially of and mounted on the heater block 70. In FIG. 5, the indicator ring 162 is shown partly broken away. Each indicating LED 160 lights in response to a change of state of the electromechanical switch 150 associated with the corresponding well 82.

A module status indicator such as LED 164 may be provided.

(For purposes of illustration, the electrical connection between the indicating LED 160 and the auxiliary board 66, and the connection between the photodetectors 126 and the auxiliary board 66, are shown as twisted pairs of leads. In practice, it is currently preferred to accomplish such connections using a flexible circuit board wrapped around the heater block.)

The electronics will now be described in detail with reference to FIGS. 7 and 8. As stated above, each module is provided with an auxiliary board 66, and the master module 20 is additionally provided with an instrument controller board 64.

The instrument controller board 64 communicates with each auxiliary board 66 through digital and analog interfaces and the instrument controller board 64 is in communication with the host computer 1 by means of a standard RS-232 digital serial interface and physical connector 165 (FIG. 6). In particular, the instrument controller board 64 controls the auxiliary board 66 via digital signals and receives analog measurements of light transmission from the measuring photodetector 126 that has been selected. Additional analog signals come from the temperature measurement circuit and from any expansion modules that may be present. Additional digital signals indicate whether expansion modules are connected.

Figure 7:
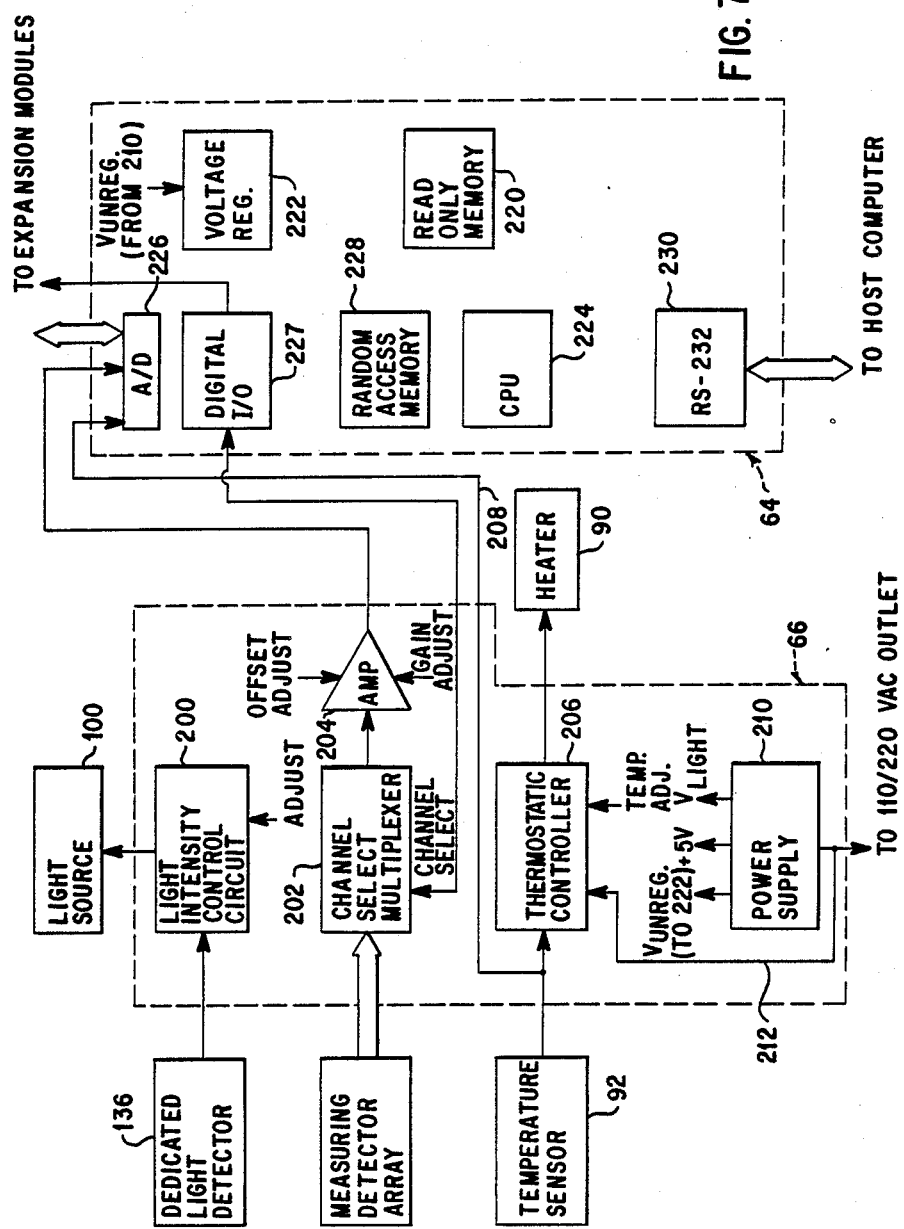
FIG. 7 is a schematic representation of the electronics resident in a master module according to the current invention and illustrating the preferred separation of components and functions between an auxiliary board and an instrument controller board.

FIG. 7 is a block diagram schematically representing the electronics of a master module 20 according to the preferred embodiment. Dashed lines are used to demarcate the auxiliary board 66 and the instrument controller board 64.

On the auxiliary board is a light intensity control circuit 200 constantly monitoring the signal from the photodetector 136 that is dedicated to measuring the light output from the measuring light source 100. The light intensity control circuit 200 constantly regulates the current to the measuring light source 100 so that the signal from the dedicated photodetector 136 remains constant. Accordingly, the controlled measuring light intensity remains constant despite any changes that may occur in the filament 106 (i.e., from aging or replacement of the bulb), the supply voltage or the ambient temperature.

A channel select multiplexer 202 is responsive to channel select commands received from the instrument controller board 64, according to which each channel (i.e., each measuring photodetector) may be interrogated once, in order, in a given cycle time. For each well 82 in which the state of the associated switch 150 indicates that a test tube 10 is present in the well, and therefore that a measurement is to be taken for that well, the signal from the measuring photodetector 126 associated with that well is amplified at 204, and the amplified analog signal is passed to the instrument controller board 64. In accomplishing this result, the switch settings are scanned and serially shifted from the auxiliary board to the controller board. If the switch is grounded, a logical zero stored in the buffer indicates that no test tube is present.

A thermostatic controller 206 on the auxiliary board 66 is responsive to the temperature sensor 92 and regulates the power to the heater 90 in order to maintain a constant temperature of the incubator 30. A separate line 208 is employed to send a signal to the instrument controller board 64 representative of the output of the temperature sensor 92.

As indicated in the figure, provisions are made to adjust the set points of the thermostatic controller 206 and the light intensity control circuit 200. Provision is also made to adjust the offset and the gain of the photodetector signal amplifier 204. Such adjustments may be provided, for example, by potentiometers on the auxiliary board 66.

Because of the overall design of the instrument, the power supply 210 may be a simple one, as will now be described.

The instrument is designed to plug into a standard wall outlet providing either 110 or 220 VAC. As shown at 212, the heater is run off this main supply voltage. In order to heat up the incubator 30 within a desirable time period and to maintain the set point temperature at 37° C., it is desirable for the heater 90 to dissipate approximately 100 watts. It also is desirable for the heater 90 to dissipate the same amount of heat regardless of whether a supply voltage of 110 or 220 VAC is used. Accordingly, the heater, which may be a simple resistive element in the form of a band, preferably includes two separate circuits, one for each operating voltage. Thus, to change over the instrument to run at 220 volts, one must change the connections on the heater band as well as the transformer of the power supply 210. If desired, switches may be provided to facilitate this change. The only regulated voltage that is required is a +5 VDC supply for the on-board CMOS integrated circuits. The measuring light source 100 and heater circuitry are self-regulating and have no special regulation requirements. This feature allows the power supply 210 to be built simply and inexpensively as part of the auxiliary board 66.

In particular, a low voltage, low wattage halogen bulb was chosen for the measuring light source 100 because of the stability of the filament 106 over long periods. Any degradation of the filament 106 over time can be compensated for by the light control circuit 200, which measures the light intensity output of the bulb and compares this information with a known reference to control the current to the bulb, as described above. The noted adjustment on the light control circuit 200 allows the light output to be regulated to any desired level. Because the light output is self-regulating, an unregulated supply for the bulb is acceptable. The power consumption of the CMOS circuits is sufficiently low that the inefficiency inherent in a three terminal series regulator is acceptable for providing the regulated 5 volt supply. The power supply transformer may be chosen so that the rectified AC voltage can provide both the unregulated voltage for the halogen bulb and the regulated 5 volts required by the electronics. (A SIGNAL LP transformer has successfully been used.) The transformer may be sized to handle the power requirements of the bulb. Because of the unregulated nature of the supply required by the bulb, separate rectifiers are used for the light and the sensor electronics.

Figure 8:
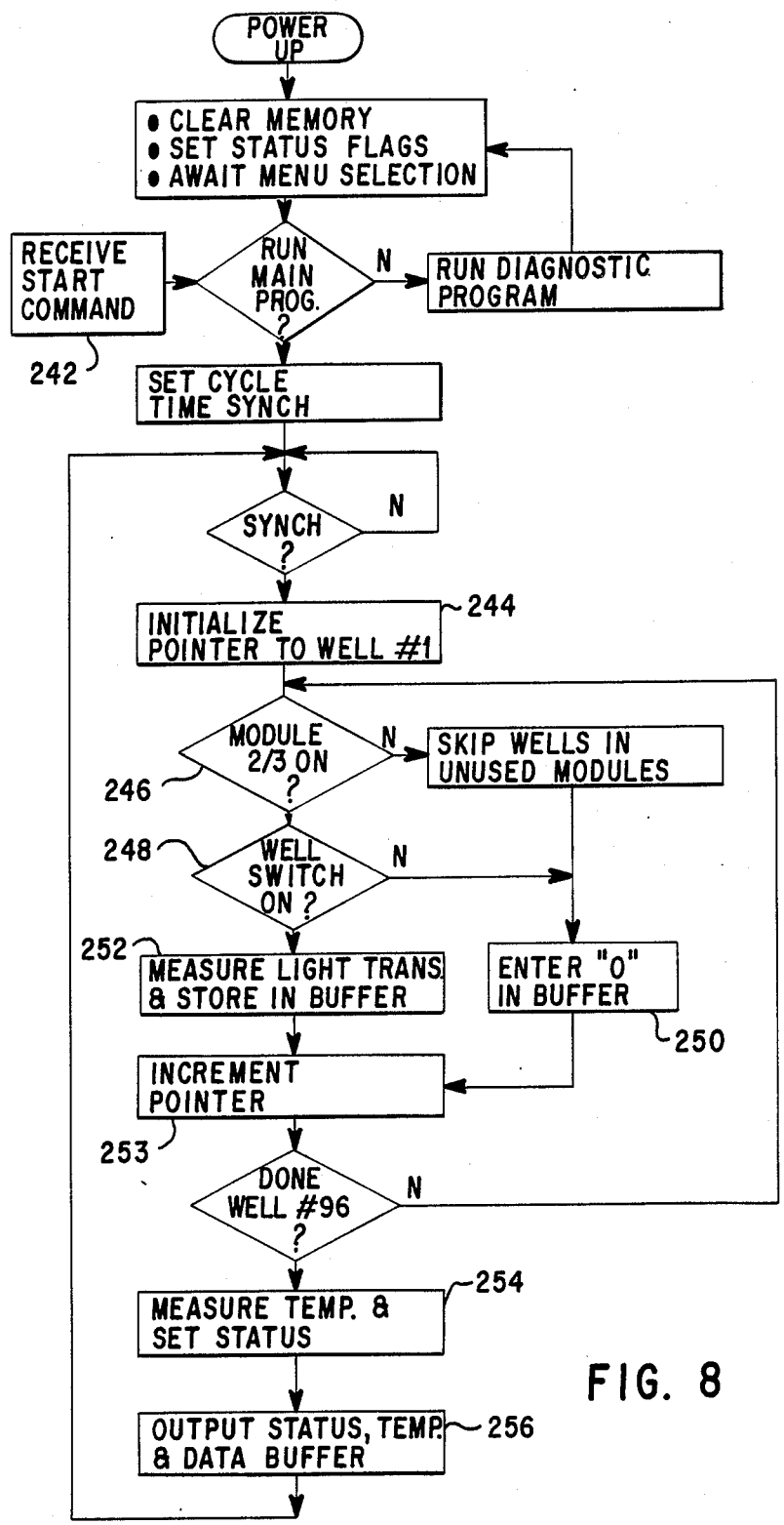
FIG. 8 is a flow chart of a program residing in memory on the instrument control board.

The instrument controller board 64 is a single board digital computer of a type commercially available from a variety of sources, to which has been added a custom ROM 220 containing a BASIC language program according to the flow chart shown in FIG. 8. A Tattletale Model 2 by Onset Computer Corp., which comes equipped with analog to digital conversion capability (see below), has successfully been used. If a different computer were selected, such capability must be added.

The board 64 contains a voltage regulator 222 for the on-board electronics, a central processing unit 224, the above-noted custom ROM 220, analog to digital converting means 226 for digitizing the analog photodetector signals received from the auxiliary board 66 of the module (and, if one or more expansion modules 22 are in use, also received from the auxiliary boards 66 of those expansion modules), a digital I/O interface 227 for communicating with the channel select multiplexer 202, memory means 228 for buffer storage of the digitized signals and related information, and an RS-232 interface represented schematically as 230 for communicating with the host computer 1 through connector 165. If desired, the A/D conversion may separately be performed on each auxiliary board 66, but the illustrated embodiment is preferred. The voltage regulator 222 receives the crude unregulated output of the transformer-based power supply 210 on the auxiliary board 66 and derives a regulated five volt supply for use on the controller board 64. For this purpose, the unregulated output of the power supply 210 may fall between six and ten volts.

Now referring to FIGS. 4 and 8, it may be seen that the host computer issues a command to start the instrument (46, 242) at which point control is substantially surrendered to the instrument controller board 64 and its resident program as shown in FIG. 8. Thereafter, the instrument controller board 64 generates the above-noted channel select signals, sending them to the auxiliary board 66 of each active module, in sequence (boxes 244, 253). The state of each well state indicating means (i.e., the electromechanical switches 150) is checked (boxes 246, 248). Such operation is repeated cyclically, for example every ten seconds, until a stop command issues from the host computer.

For each well 82 in which the state of the switch indicates that a test tube is not present, a "zero" value is stored in the buffer in a location corresponding to that particular well (box 250). For each well 82 in which the switch indicates that a test tube is present, the output from the corresponding photodetector is sent to the instrument controller board, digitized and stored in the memory buffer in a location corresponding to that well (box 252). For each such cycle, incubator temperature and status also are stored in the buffer (box 254). Accordingly, a value is stored in the buffer for every well. Each well is automatically identified by its place in the buffer. At predetermined intervals, the buffer is transmitted to the host computer (boxes 256, 48). Because the time interval is fixed, the data arriving at the host computer is in a consistent easy-to-handle format and, overall, is less voluminous than in the LAL-4000. Furthermore, because the buffer size is fixed, testing and maintenance are simplified.

It should be noted that the program resident in the instrument controller board 64 as represented by FIG. 8 is not specific to any particular kind of assay. Working together, the instrument controller 64 and the auxiliary board or boards 66 broadly perform the function of obtaining kinetic measurements from a plurality of independent channels and storing the information in digital form so that it may be passed to a host computer. All processing of the raw data is accomplished in the host computer. This practice simplifies the resident program in the instrument controller board 64, making it useful with a variety of assays.

During the data collection phase, each channel is treated independently. That is, the output of a given measuring photodetector 126 of an active channel will be stored during a cycle without regard to whether or not that channel was active during the previous cycle. Accordingly, in conducting an assay, the operator may insert test tubes 10 into the wells 82 in any order and at different times. For a given sample, the data collection begins when the test tube is inserted and changes the state of a switch 150. Thereafter, the data collected from that channel jumps from its previous zero value (that previous zero value arrising from the fact that the channel was previously inactive) to a finite value based upon the output of the photodetector 126 for that channel. When the host computer interprets the collected data, it assumes that a measurement began at "time zero" for a particular channel when the stored value for that channel jumps from zero to a finite value.

Additional characteristics and advantages of an instrument according to the current invention will now be described.

As noted above, some previous instruments have employed a plurality of separate light sources and detectors for each test tube. Such arrangement has the disadvantage that it is difficult to manipulate the strength and spectral qualities of the individual light sources and further makes it difficult to use filters and differing light sources in an attempt to conduct chromogenic assays. Other instruments, such as the microplate reader, sequentially move a plurality of samples past a single light source/detector pair. This approach requires moving parts, giving rise to at least two detrimental effects. First, the poor optical properties of the test tubes make it difficult to achieve repeatable results. Second, the resulting agitation affects the reaction rate. In addition, the microplate reader has the additional disadvantage that all the samples must be prepared at one time. The tests are not independently initiated.

In contrast is an instrument according to the current invention in which the individual tubes are fixed and which employs a single light source that offers the potential to be used in any of a variety of assays.

In addition, the test tube wells of an instrument according to the current invention are arranged in a circle, each well being equidistant from a single light source. Among the advantages of such an arrangement are the following:

The total circuitry associated with light generation is reduced, because only one measuring light source is present in any given module.

A single dedicated photodetector is used to monitor and correct for any variability in the light source (e.g., due to aging or temperature) or in the supply voltage. This self-regulation reduces the complexity of the power supply. It is important to note that, because all photodetectors "see" the same light source, any variability in the light source will be common to all detectors, thereby enhancing the ability of the instrument and the host computer to make comparative measurements between standard samples and unknown samples.

Unlike many other instruments, the electronic parts associated with the incubator are easily accessible. This is especially true of both the light source and the photodetectors.

A variety of light sources and filters may readily be used. Accordingly, an instrument according to the current invention may be used as a spectrophotometer.

Figure 1:
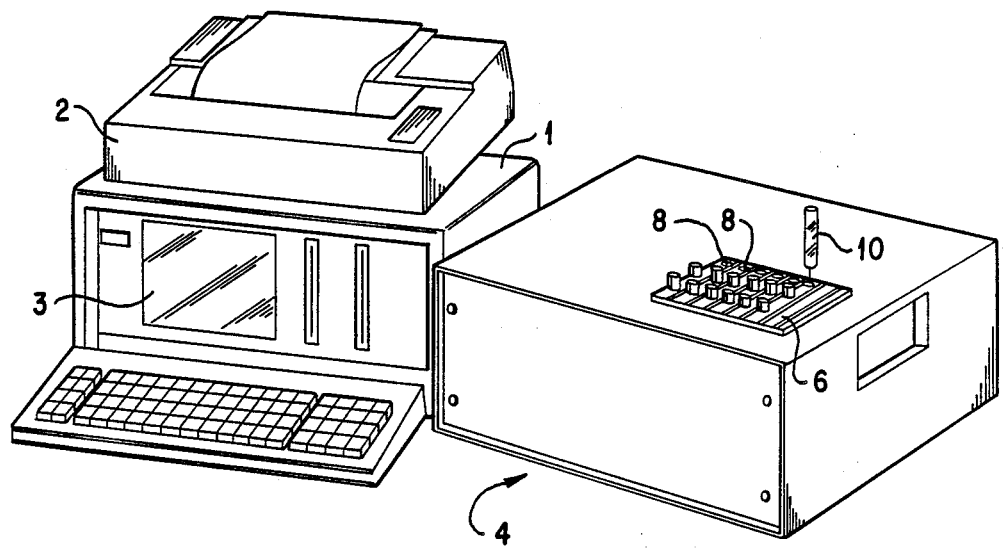
FIG. 1 is a pictorial view of a prior art system including a LAL-4000 analytic instrument.
Figure 2:
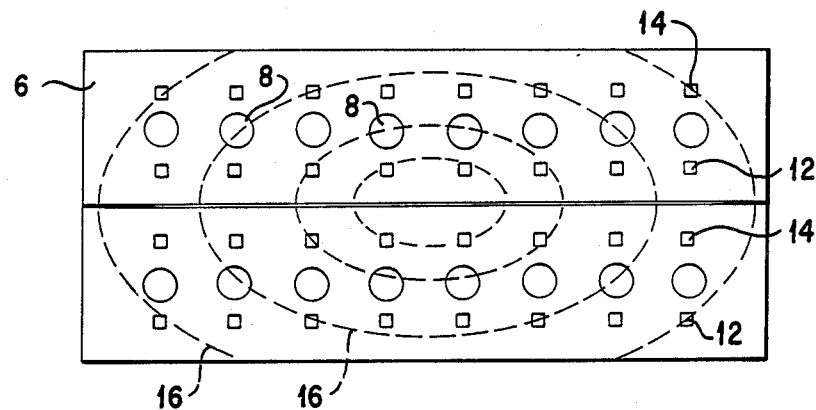
FIG. 2 is a diagram showing the thermal gradients in an incubator block of the LAL-4000, when seen from above.
Figure 9:
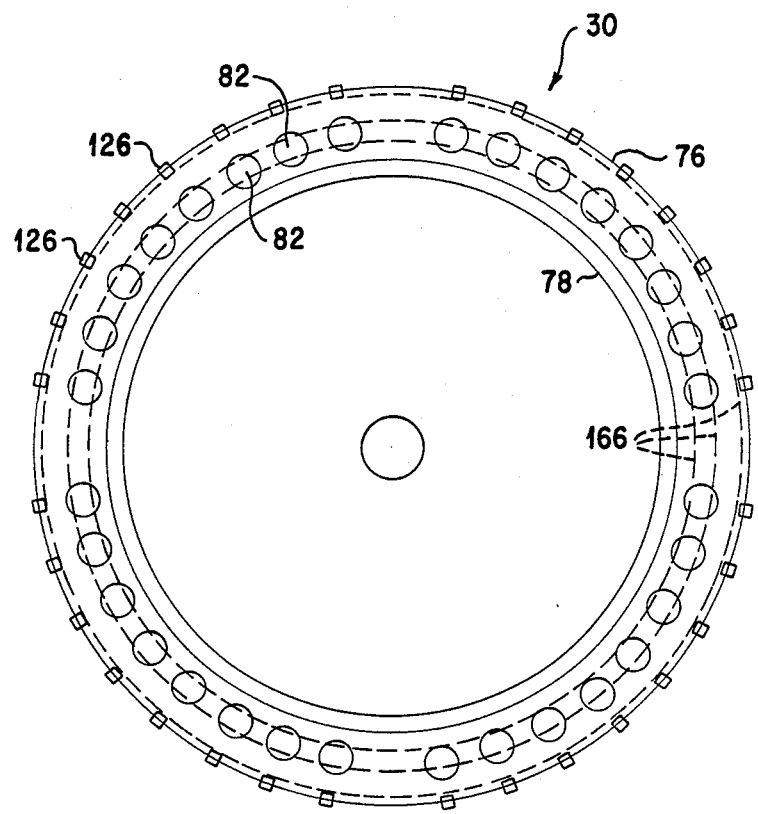
FIG. 9 is a view representing the thermal gradients in an incubator block according to the current invention, when viewed from above.

Many assays, including the LAL assay, are sensitive to temperature. In particular, the rate at which a reaction progresses during an assay frequently is a function of temperature. To minimize error due to temperature variation, some prior instruments have attempted to control the temperature of the incubator. However, as noted above in regard to FIG. 2, a source of error can arise from a variability in temperature from one well to the next due to gradients within the incubator, and the thermal gradient is not consistent when using the rectangular array of wells found in prior instruments. FIG. 9 is a diagrammatic top view of an incubator 30 according to the current invention, the diagram showing thermal gradients represented in dashed lines by isotherms 166. The energy from the heater is applied uniformly circumferentially of the heater block, so that each well 82 is disposed on an isotherm. Furthermore, because the wells are equidistant from a single light source, any thermal effect arising from the incandescent light source uniformly affects each well. Accordingly, all samples are at the same temperature.

It has been noted above that mounting the photodetectors 126, 136 in close thermal contact with the incubator, in general, controls the temperature of the photodectors to the overall or approximate temperature of the incubator, thereby eliminating sources of error. Now, it may be additionally seen that, due to the above-noted circular symmetry of the instrument, each photodetector is mounted on an isotherm so that all of them are at the same temperature. This is true even of the dedicated photodetector 136 that is used to regulate the measuring light source. Accordingly, sources of error arising from temperature differences among the various photodetectors are even further reduced.

The use of a single light source in combination with a separate photodetector for each sample enables the use of test tubes made of inexpensive, non-optical grade glass. Furthermore, no moving parts such as a carousel are required to move the samples past a detector (as in the Coagamate), thereby allowing for the reading of a large number of samples in short time intervals and avoiding motion that would disturb the samples during assays that employ turbidity measurements.

From a manufacturing perspective, it is easier and less expensive to machine round pieces on a lathe than square ones on a milling machine. Accordingly, the heater block 70 and test tube racks 80 according to the current invention are comparatively inexpensive to manufacture.

As noted above, the arrangement of the invention allows for the use of a diffuser. This has the advantage of improving the radial symmetry of the light emitted from the source. Because only relative changes in light measured at each measuring detector are important, radial symmetry of the light output is not critical. However, improving the radial symmetry provides the significant advantage of allowing better resolution of the A/D converter.

In the current invention, the measuring light source provides a constant output. In prior inventions, pulsed light sources are often used for detecting absolute light levels, first by measuring an ambient light level and subtracting the results during test from the ambient level. In the current invention, only relative changes in light transmission are required. Accordingly, a pulsed light source is unnecessary. Use of a continuous light source simplifies the circuitry and extends the life of the bulb.

As has been noted above, the test tube retaining ring 86 constrains the test tubes in order to minimize the effects of jarring on the detector output. In addition, the use of the retaining ring allows the diameters of the test tube wells to be made slightly larger than has been done in the past, for example than in the LAL-4000. In particular, the disposable test tubes are made with a large tolerance, and many tubes cannot fit in the wells of the LAL-4000. The result is that the operator of the LAL-4000 must expend time to pre-select and sort those test tubes which fit the wells, discarding the ones that do not fit. Accordingly, the current invention can accommodate test tubes with a large variability in their dimensions. A retainer ring of the type shown would be more difficult to incorporate in a heater block assembly having test tubes arranged in a rectangular grid.

The intelligent division of functions provided by the current invention between the host computer, the instrument controller board and the auxiliary board provides distinctive advantages over prior instruments. With specific regard to the auxiliary board or boards, it should be noted that the measurement collection function performed thereby is essentially passive, except for the switching function performed by the channel select electronics as instructed by the instrument controller. Accordingly, in terms of data gathering, the auxiliary board does little more than obtain and amplify the signal from selected measuring photodetectors and pass the amplified analog signal to the instrument controller. By thus minimizing the functions performed by the auxiliary board, the cost of an expansion module is kept lower, the expansion module may be more compact, have lighter weight and, importantly, be more versatile. Such versatility results from the fact that the functions performed by the auxiliary board are not specific to a particular kind of assay.

Similar considerations also pertain to a master module, which also includes an instrument controller board. Such a module may have a volume as least as low as 680 cubic inches and a weight at least as low as 12 lbs. A currently preferred embodiment is about thirteen inches wide, ten and one half inches deep, and about six inches in height. Although the data gathering function performed by the instrument controller board is not as passive as that performed by the auxiliary boards, it nevertheless is true that the program resident in the instrument controller board is not specific to any particular kind of assay. Therefore, in terms of data gathering, the instrument electronics are primarily a means of gathering, digitizing and storing raw data. All processing of raw data is accomplished in the host computer, which can run a variety of assay-specific programs. The program selected for running in the host computer will correspond to the type of assay being conducted. This feature both greatly simplifies the program resident in the instrument controller board and also enhances the versatility of the instrument as a whole, making it usable with other assays. Indeed, a laboratory having possession of the instrument and a host computer is given a great variety of options in how it wishes to employ the raw data passed by the instrument to the host computer, inasmuch as the software for the host computer is more easily subject to such modification as may be desired.

Thus it may be seen that the current invention broadly provides a highly versatile instrument for independently and kinetically measuring light transmission through a plurality of samples by obtaining output signals from a plurality of photodetectors and for digitizing and storing those signals and making them available to a host computer, without express regard to the specific ultimate use to be made of the stored information by the host computer. It is thought to be the first instrument for kinetically measuring the light absorption characteristics of a plurality of independent samples in disposable test tubes arranged in a circular pattern about a single light source.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A kinetic analytical instrument having a plurality of independent channels for obtaining output data from a plurality of photodetectors resulting from changes in light transmission through a plurality of samples, said instrument comprising at least a first module, said first module comprising:

a stationary first housing;

first test tube support means substantially fixedly mounted within said first housing and having formed therein a plurality of wells disposed in a substantially circular array and a first plurality of light passages respectively disposed transversely of and intersecting said plurality of wells, each of said plurality of wells being adapted to receive a test tube, said first test tube support means comprising means for respectively fixedly supporting a plurality of test tubes in said plurality of wells and in a substantially circular array wherein said test support means comprises an incubator of a substantially annular shape centered on a center of curvature of said circular array of wells, said incubator including a heater block and further comprising heater means for heating said incubator block, said incubator further including a test tube rack having said wells formed therein and being in the form of a substantially annular block, said heating block having formed therein a receiving opening receiving said test tube rack and wherein said means for fixedly supporting said plurality of test tubes comprises biasing means for biasing test tubes in said wells against interior walls of said wells, said biasing means comprising an elastic ring-like member disposed radially outside said circular array of wells;

a single first measurement constant output light source centrally mounted within said first housing and being so disposed that light radially emitted therefrom passes through each of said first plurality of light passages and traverses each of said plurality of wells, said first measurement light source being disposed substantially equidistant from each of said plurality of wells;

a plurality of measuring photodetectors disposed in said first housing and respectively fixedly mounted with respect to each of said first light passages so as to each receive light from said first measurement light source after said light has traversed said plurality of wells and said plurality of samples and for independently and kinetically measuring light transmission through said plurality of samples while controlling a plurality of variable; and instrument control means programmed to provide a series of channel select signal.

2. An instrument according to claim 1, said heater block having at least one curved sidewall concentric with said circular array of wells and being disposed therearound.

3. An instrument according to claim 2, further comprising heater power supply means for said heater means and temperature sensing means for sensing a temperature of said heater block, wherein said heater power supply means comprises means responsive to said temperature sensing means for regulating the energy supplied to said heater means so that the temperature of said heater block remains substantially constant.

4. An instrument according to claim 3, wherein said measuring photodetectors are mounted on said incubator in close thermal contact therewith, said heater means and the mass of said incubator collectively comprising means for maintaining each said measuring photodetector at substantially the same constant temperature.

5. An instrument according to claim 1, there being a slot formed in and extending circumferentially of said test tube rack, said ring-like member being received in said slot.

6. An instrument according to claim 1, wherein a plurality of said wells have circular cross-sections have diameters substantially in the range between 0.394 inches and 0.399 inches.

7. An instrument according to claim 1, wherein each of said plurality of wells have circular cross-sections have diameters substantially in the range between 0.470 inches and 0.475 inches.

8. An instrument according to claim 1, wherein said measurement light source is disposed at a center of curvature of said substantially circular array of wells.

9. An instrument according to claim 8, further comprising a control photodetector fixedly mounted so as to receive light from said measuring light source, said power supply means for said measurement light source comprising measurement light regulating means responsive to a signal from said control photodetector for continuously regulating an output of said measurement light power supply so that said signal from said control photodetector remains substantially constant.

10. An instrument according to claim 1, comprising:
first module control means disposed in said first housing and comprising at least:
first power supply means for said first measurement light source;
first well state indicating means associated with a plurality of said first wells for providing an independent indication for each first well indicating whether or not a measurement is to be taken for that well; and
first photodetector interrogating means responsive to said stepping signals for passing an output signal to said instrument control means from each first measuring photodetector that is associated with a first well for which said indication of said first well state indicating means indicates that a measurement is to be taken for that well.

11. An instrument according to claim 10, wherein said control photodetector and said measuring photodetectors are mounted on said test tube support means in close thermal contact therewith, wherein the temperature of said control photodetector will remain substantially equal to the temperatures of said measuring photodetectors.

12. An instrument according to claim 8, further comprising light diffuser means disposed between said measurement light source and said wells.

13. An instrument according to claim 8, further comprising spectrally-selective light filter means disposed between said measurement light source and said wells.

14. An instrument according to claim 10, said well state indicating means comprising a plurality of electromechanical switches respectively associated with a corresponding plurality of said wells, each said switch having actuator means extending into its corresponding well and disposed for being contacted by a test tube present within said corresponding well, wherein the introduction of a test tube into a well causes a change of state of the switch that is associated therewith, said photodetector interrogating means being independently responsive to the state of each said switch.

15. An instrument according to claim 1, wherein said programmed instrument control means includes at least a central processing unit and memory means, said instrument further comprising digitizing means for digitizing said signals from said measuring photodetectors, said instrument control means being programmed to store said digitized signals in said memory means.

16. An instrument according to claim 15, said instrument control means further comprising interface means for communicating said instrument control means with a host computer.

17. An instrument according to claim 10 further comprising at least a second module, said second module comprising:
a second housing;
second test tube support means substantially fixedly mounted within said second housing and having formed therein an additional plurality of wells disposed in a substantially circular array and a second plurality of light passages respectively disposed transversely of and intersecting said additional wells, each of said additional wells being adapted to receive a test tube, said second test tube support means comprising means for supporting a plurality of test tubes at fixed locations and in a second substantially circular array;
a single second measurement light source mounted within said second housing and being so disposed that light therefrom will pass through each said second light passage and will traverse each of said additional wells, said second measurement light source being disposed substantially equidistant from each of said additional wells;
a second plurality of measuring photodetectors disposed in said second housing and respectively fixedly mounted with respect to said second light passages so as to receive light from said second measurement light source after said light has traversed said additional wells; and
second module control means disposed in said second housing and comprising at least:
second power supply means for said second measurement light source;
additional well state indicating means associated with a plurality of said additional wells for providing an independent indication for each of said second wells indicating whether or not a measurement is to be taken for that well; and
second photodetector interrogating means responsive to said stepping signals for sequentially and repeatingly passing an output signal to said instrument control means from each second measuring photodetector that is associated with one of said additional wells for which said indication of said additional well state indicating means indicates that a measurement is to be taken for that well.

18. An instrument according to claim 17, wherein said instrument control means is disposed in one of said first and second modules and is in communication with said first and second module control means, said instrument control means including at least a central processing unit and memory means, said instrument further comprising digitizing means for digitizing said signals from said measuring photodetectors, said instrument control means being programmed to access said first and second module control means and to store said digitized signals in said memory means.

19. An instrument according to claim 18, further comprising interface means for communicating said instrument control means with a host computer.

* * * * *